United States Patent
Sumi et al.

(10) Patent No.: US 11,535,595 B2
(45) Date of Patent: Dec. 27, 2022

(54) ISOQUINOLINE SULFONYL CHLORIDE ACID ADDITION SALTS AND METHOD OF MANUFACTURE THEREOF

(71) Applicant: D. WESTERN THERAPEUTICS INSTITUTE, INC., Nagoya (JP)

(72) Inventors: Kengo Sumi, Nagoya (JP); Ryohei Nakamura, Nagoya (JP)

(73) Assignee: D. WESTERN THERAPEUTICS INSTITUTE, INC., Nagoya (JP)

( * ) Notice: Subject to any disclaimer, the term of this patent is extended or adjusted under 35 U.S.C. 154(b) by 0 days.

(21) Appl. No.: 17/296,469

(22) PCT Filed: Dec. 16, 2019

(86) PCT No.: PCT/JP2019/049100
§ 371 (c)(1),
(2) Date: May 24, 2021

(87) PCT Pub. No.: WO2020/129877
PCT Pub. Date: Jun. 25, 2020

(65) Prior Publication Data
US 2021/0395205 A1 Dec. 23, 2021

(30) Foreign Application Priority Data

Dec. 18, 2018 (JP) .............................. JP2018-236372

(51) Int. Cl.
*C07D 217/22* (2006.01)
*C07D 217/02* (2006.01)

(52) U.S. Cl.
CPC ......... *C07D 217/22* (2013.01); *C07D 217/02* (2013.01)

(58) Field of Classification Search
CPC ............................ C07D 217/22; C07D 217/02
See application file for complete search history.

(56) References Cited

U.S. PATENT DOCUMENTS

| | | |
|---|---|---|
| 2005/0267152 A1 | 12/2005 | Bloomfield et al. |
| 2006/0199816 A1* | 9/2006 | Gillespie ................. A61P 43/00 514/319 |
| 2009/0209765 A1 | 8/2009 | Sakai et al. |
| 2012/0035159 A1 | 2/2012 | Hidaka et al. |
| 2013/0150339 A1 | 6/2013 | Boezio et al. |
| 2013/0274269 A1* | 10/2013 | Hidaka ................... A61P 27/02 546/139 |
| 2014/0288081 A1 | 9/2014 | Cianchetta et al. |
| 2019/0169166 A1 | 6/2019 | Fujimoto et al. |

FOREIGN PATENT DOCUMENTS

| | | |
|---|---|---|
| CA | 1 218 646 A | 3/1987 |
| CN | 103739525 | 4/2014 |
| EP | 2 444 395 A1 | 4/2012 |
| EP | 2 657 227 A1 | 10/2013 |
| JP | 60-48936 A | 3/1985 |
| JP | 7-247246 A | 9/1995 |
| JP | 10-36326 A | 2/1998 |
| JP | 2005-519048 A | 6/2005 |
| JP | 2016-512203 A | 4/2016 |
| WO | WO 2006/090783 A1 | 8/2006 |
| WO | WO 2010/146881 A1 | 12/2010 |
| WO | WO 2012/086727 A1 | 6/2012 |
| WO | WO 2018/030466 A1 | 2/2018 |
| WO | WO 2020/091054 A1 | 5/2020 |

OTHER PUBLICATIONS

International Search Report dated Jan. 28, 2020 in PCT/JP2019/049100 filed on Dec. 16, 2019, 3 pages.

Weiss et al., "Sulfonamides as Selective $Na_v1.7$ Inhibitors: Optimizing Potency and Pharmacokinetics While Mitigating Metabolic Liabilities", Journal of Medicinal Chemistry, 2017, vol. 60, pp. 5969-5989.

Marciniec et al., "Synthesis, Anti-Breast Cancer Activity, and Molecular Docking Study of a New Group of Acetylenic Quinolinesulfonamide Derivatives", Molecules, 2017, vol. 22, pp. 1-19.

Extended European Search Report dated Jun. 14, 2022, in corresponding European Patent Application No. 19900110.8, 14 pages.

Yu-Ming Pu, et al., "A simple and highly effective oxidative chlorination protocol for the preparation of arenesulfonyl chlorides", Tetrahedron Letters, vol. 51, No. 2, XP27259073A, Jan. 13, 2010, pp. 418-421.

Véronique Leclerc, et al., "Design and synthesis of naphthalenic derivatives as new ligands at the melatonin binding site $MT_3$", European Journal of Medicinal Chemistry, vol. 46, No. 5, XP28370928A, Feb. 8, 2011, pp. 1622-1629.

Philip J. Hogan, et al., "Aqueous Process Chemistry: The Preparation of Aryl Sulfonyl Chlorides", Org. Process Res. Dev., vol. 13, No. 5, XP55900956A, Sep. 18, 2009, pp. 875-879.

* cited by examiner

*Primary Examiner* — Timothy R Rozof
(74) *Attorney, Agent, or Firm* — Oblon, McClelland, Maier & Neustadt, L.L.P.

(57) ABSTRACT

A compound, such as isoquinoline-6-sulfonyl chloride acid and/or addition salts thereof, may be useful as a manufacturing intermediate for an isoquinoline-6-sulfonamide compound. A method for manufacturing such compounds and/or or acid addition salts thereof, may involve subjecting 6-(benzylthio)isoquinoline to an oxidative chlorination reaction and/or reacting 6-aminoisoquinoline with a nitrite or nitrous acid ester, then with thionyl chloride, and then with an acid.

17 Claims, 4 Drawing Sheets

ISOQUINOLINE SULFONYL CHLORIDE ACID ADDITION SALTS AND METHOD OF MANUFACTURE THEREOF

CROSS-REFERENCE TO RELATED APPLICATIONS

The present application is the national stage of international application PCT/JP2019/049100, filed on Dec. 16, 2019, and claims the benefit of the filing date of Japanese Appl. No. 2018-236372, filed on Dec. 18, 2018.

FIELD OF THE INVENTION

The present invention relates to an isoquinoline-6-sulfonyl chloride acid addition salts that are useful as a pharmaceutical manufacturing intermediate and a method for their manufacture.

BACKGROUND OF THE INVENTION

Patent Documents 1 and 2 disclose that an isoquinoline-6-sulfonamide compound is useful as an active ingredient of a pharmaceutical for preventing or treating glaucoma, ocular hypertension, cardiovascular disease, or a disease or disorder caused by nerve degeneration or nerve injury. It is also disclosed that isoquinoline-6-sulfonyl chloride (compound (1)) is used as a key intermediate to manufacture the sulfonamide compound and can be synthesized from a diazonium salt of 6-aminoisoquinoline (3) as shown by the following formula:

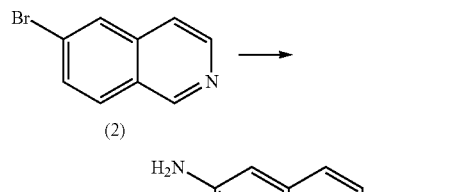

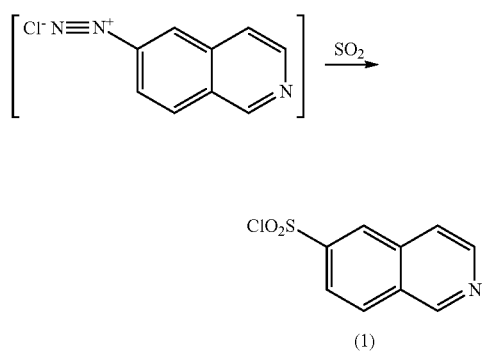

CITATION LIST

Patent Document

Patent Document 1: International Patent Publication 2010/146881

Patent Document 2: International Patent Publication 2012/086727

SUMMARY OF THE INVENTION

Technical Problem

This method, however, is unfavorable as an industrial manufacturing method in some aspects, including the passage of a route via an unstable diazonium salt and the use of sulfurous acid gas. Furthermore, while the aforementioned patent documents disclose a method involving the use of compound (1) in solution, without purification after the reaction, in the next reaction, in consideration of its instability, the method is evidently disadvantageous from the viewpoint of pharmaceutical manufacture under strict control because of a concern that such operations can lead to decreased reaction efficiency, decreased quality of the final product, and other drawbacks due to impurities contained in the solution, the inability to calculate the appropriate equivalents of reagents and raw materials used in the next step, and other facts. In addition, 6-aminoisoquinoline (3), used as a precursor, is also obtained by reacting 6-bromoisoquinoline (2) with aqueous ammonia at high temperature and high pressure; these conditions are extremely severe, posing a problem with safety and operability.

Hence, no disclosure has so far been available of any appropriate manufacturing method or purification method for compound (1) to be used as a pharmaceutical manufacturing intermediate, nor has there been any demonstration.

In general, the purify of a pharmaceutical manufacturing intermediate significantly influences the quality of the final product; therefore, there is a high demand for a convenient and highly efficient manufacturing method for obtaining a highly pure intermediate in each step.

Accordingly, the present invention is intended to provide a new industrially advantageous form of compound (1) and a method of its manufacture, for obtaining compound (1), with high quality, that is to be used as an intermediate to obtain, with high quality, an isoquinoline-6-sulfonamide compound that is useful as an active ingredient of a pharmaceutical.

Solution to Problem

The present inventors first attempted to isolate and purify compound (1) from an extract solution in an aftertreatment following the aforementioned reaction. When the extract solution containing compound (1) was concentrated under reduced pressure, and the resulting crude product was purified by silica gel column chromatography, it was found that the percent recovery remained at an extremely low level of 8%. Hence, as pointed out in Patent Documents 1 and 2, it was strongly suggested that the aforementioned isolation and purification operations should be avoided. Judging from this result, it was considered that compound (1) occurred in a relatively stable state in the post-extraction organic solvent in the aftertreatment but decomposed or degraded during isolation and purification, which in turn can lead to decreased percent recovery. In fact, it was confirmed that compound (1) degraded or decomposed on a silica gel thin-layer chromatography (TLC) plate in test examples described below.

Taking this situation into account, the present inventors considered that the use of compound (1) as an appropriate intermediate for pharmaceutical manufacturing required further investigations, including a method for its manufacture.

The present inventors attempted to acquire compound (1) using an oxidative chlorination method with benzylthio compound (4), which can be prepared from 6-bromoisoquinoline (2) in one step, as a precursor, so as to establish a convenient and industrially applicable method for producing compound (1). This method was proven to allow chlorosulfonylation to proceed efficiently. Since the crude product obtained in the aftertreatment following this reaction was found to contain many impurities, further purification was considered necessary. However, purification by silica gel column chromatography cannot be used because it is likely to extremely reduce the percent recovery of compound (1) as described above, and it is not practical for industrialization. On the other hand, purification by recrystallization might be feasible, which, however, involved a concern about the stability of compound (1) when heating is required, and a possibility of decreased percent recovery due to an increase in the amount of solvent used to increase the purity. In all cases, there was a concern about hydrolysis of compound (1) because of the use of an aqueous solution of sodium hydrogen carbonate in the aftertreatment following this reaction.

Hence, the present inventors conducted various investigations, finding that compound (1) can be stably isolated in the forms of acid addition salts, rather than as a free form, to markedly improve the purification efficiency. The present inventors also found that a highly pure isoquinoline-6-sulfonamide compound is obtained at a high percent recovery with the use of the acid addition salts of compound (1), and completed the present invention.

Accordingly, the present invention provides substances and methods described in the following terms [1] to [6]:

[1] Isoquinoline-6-sulfonyl chloride acid addition salts.

[2] The acid addition salts described in term [1] above, wherein the acid is hydrochloric acid, hydrobromic acid, sulfuric acid, or phosphoric acid.

[3] A manufacturing method for isoquinoline-6-sulfonyl chloride or acid addition salts thereof, comprising subjecting 6-(benzylthio)isoquinoline to an oxidative chlorination reaction.

[4] A manufacturing method for isoquinoline-6-sulfonyl chloride acid addition salts, comprising reacting 6-aminoisoquinoline with a nitrite or nitrous acid ester, then with thionyl chloride, and then with an acid.

[5] A manufacturing method for an isoquinoline-6-sulfonamide compound, comprising reacting an isoquinoline-6-sulfonyl chloride acid addition salt with an amine compound.

[6] 6-(Benzylthio)isoquinoline.

Effect of the Invention

The isoquinoline-6-sulfonyl chloride acid addition salts of the present invention can be easily and inexpensively obtained from a commonly known compound and can be isolated as a highly pure salt. In addition, with the use of isoquinoline-6-sulfonyl chloride acid addition salts, it is possible to manufacture an isoquinoline-6-sulfonamide compound that is useful as a highly pure pharmaceutical, in an industrially advantageous manner.

DETAILED DESCRIPTION OF THE INVENTION

Figure 1:
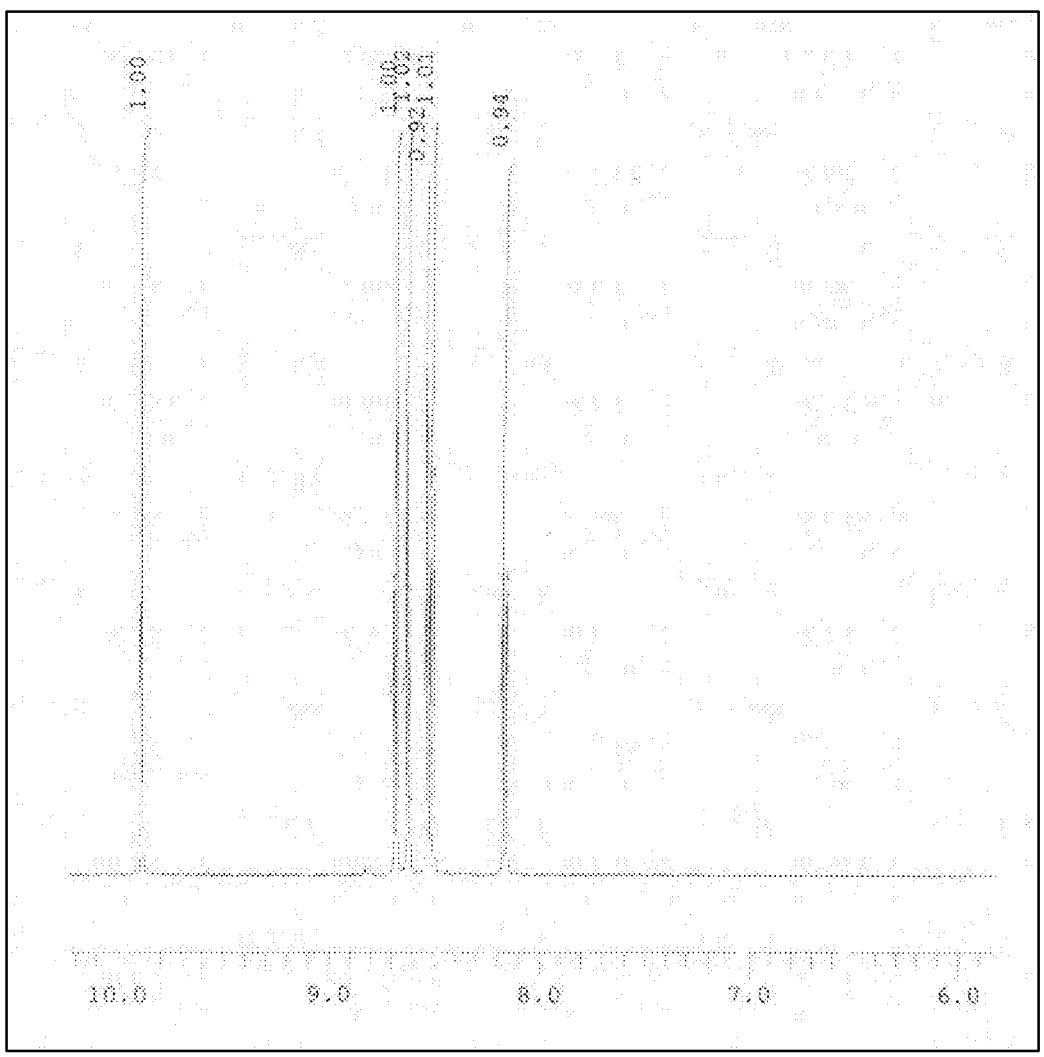
FIG. 1 shows a $^1$H NMR chart of the isoquinoline-6-sulfonyl chloride hydrochloride obtained in Example 2.

The isoquinoline-6-sulfonyl chloride acid addition salts of the present invention are represented by the following formula (5) (compound (5)):

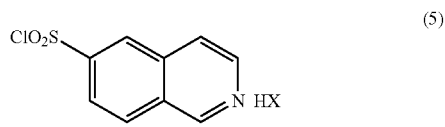

(5)

wherein HX represents an acid.

The acid represented by HX is exemplified by inorganic acids such as hydrochloric acid, sulfuric acid, nitric acid, phosphoric acid, hydrofluoric acid, and hydrobromic acid; and organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, and camphor sulfonic acid. In particular, inorganic acids such as hydrochloric acid, sulfuric acid, phosphoric acid, and hydrobromic acid are preferred, with greater preference given to hydrochloric acid.

The manufacturing method of the present invention for isoquinoline-6-sulfonyl chloride acid addition salts (5) (compound (5)) and the manufacturing method for isoquinoline-6-sulfonamide compound (6) (compound (6)) with compound (5) as an intermediate are represented by the following reaction formulas:

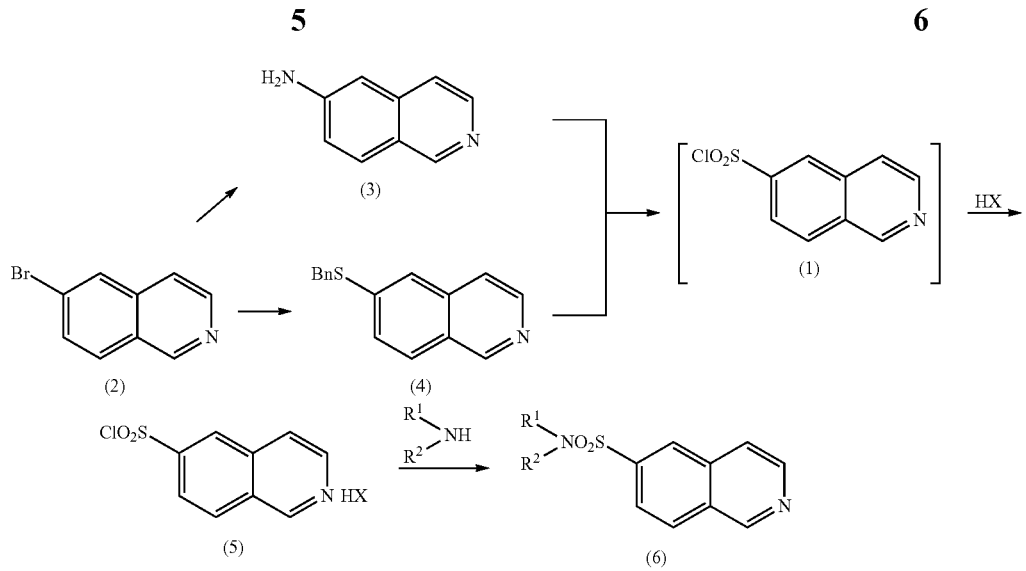

wherein Bn represents a benzyl group; HX represents an acid; $R^1$ and $R^2$ each represent a hydrogen atom or an organic group.

Compound (1) or compound (5) can be manufactured by subjecting 6-(benzylthio)isoquinoline (4) (compound (4)) to an oxidative chlorination reaction.

Here, 6-(benzylthio)isoquinoline (4) is obtained by reacting 6-bromoisoquinoline (2) with benzylmercaptan in the presence of a base in an organic solvent. 6-(Benzylthio) isoquinoline (4) is a novel compound. It is preferable that the reaction of compound (2) and benzylmercaptan be carried out in the presence of, for example, a base such as tert-butoxide potassium, potassium carbonate, or sodium hydride. Acceptable reaction conditions involve the use of a polar solvent such as dimethyl sulfoxide in which the reaction is carried out at room temperature to 150° C. for from 1 to 10 hours.

The oxidative chlorination reaction of compound (4) can be carried out by reacting compound (4) with an oxidative chlorinating agent such as 1,3-dichloro-5,5-dimethylhydantoin, sulfuryl chloride, N-chlorosuccinimide, gaseous chlorine, or sodium hypochlorite. The reaction is preferably carried out in a polar solvent such as acetic acid-acetonitrile-water under mild conditions, e.g., at room temperature or lower, for from 1 to 5 hours.

The oxidative chlorination reaction of compound (4) produces compound (1), and compound (5) may be precipitated by adding an acid to the post-reaction solution without isolation of compound (1). Specifically, an ether solvent or a hydrocarbon solvent is added to the post-reaction solution, an excess amount of an acid is directly added, and the resulting precipitate is filtered to obtain compound (5) as a purified product. The amount of acid used preferably ranges from 1 to 10 equivalents, more preferably from 1 to 3 equivalents. The amount of solvent added is preferably from 1 to 10 times, more preferably from 1 to 5 times, the amount of the reaction solution. The ether solvents that can be used here include diethyl ether and methyl tert-butyl ether. The hydrocarbon solvents include hexane. These reactions can be carried out at from 0° C. to room temperature, preferably at 0° C.

Compound (5) can also be manufactured by reacting 6-aminoisoquinoline (3) (compound (3)) with a nitrite or nitrous acid ester, then with thionyl chloride, and then with an acid.

The reaction of compound (3) and a nitrite or nitrous acid ester is a diazotization reaction. Examples of the nitrite used include metal nitrites, such as sodium nitrite and potassium nitrite, and ammonium nitrite. Examples of the nitrous acid ester include nitrous acid alkyl esters such as methyl nitrite. The reaction of compound (3) and the nitrite or nitrous acid ester is carried out in an acidic aqueous solution, and usually progresses quickly at from 0° C. to room temperature.

Next, the resulting diazonium compound is reacted with thionyl chloride to obtain compound (1). This reaction is carried out by reacting a mixture of thionyl chloride and water in an acidic aqueous solution in the presence of copper chloride at from 0° C. to room temperature for from 1 to 5 hours. This reaction is preferably carried out without isolation of the diazonium compound.

Next, the resulting compound (1) can be prepared as an acid addition salt without isolation. An acid may be added to the post-reaction solution or a solution neutralized after the reaction to precipitate compound (5). Specifically, an excessive amount of an acid is added to the reaction liquid, an ether solvent or a hydrocarbon solvent is added, and the resulting precipitate is filtered to obtain compound (5) as a purified product. The amount of acid added preferably ranges from 1 to 10 equivalents, more preferably from 1 to 3 equivalents. The amount of solvent added is preferably from 1 to 10 times, more preferably from 1 to 5 times, the amount of the reaction solution. The ether solvents that can be used here include diethyl ether and methyl tert-butyl ether. The hydrocarbon solvents include hexane. These reactions can be carried out at from 0° C. to room temperature, preferably at 0° C.

Because compound (5) can be obtained with high purity simply by adding an acid to compound (1) in the reaction solution, and then performing a simple filtration operation, as described above, there is no need for purification operations such as by extraction, column chromatography, and recrystallization.

By reacting compound (5) with an amine compound $(R^1(R^2)NH)$, isoquinoline-6-sulfonamide compound (6), which is useful as a pharmaceutical, can be manufactured. Here, examples of the amine compound represented by $R^1(R^2)NH$ include the compounds described in the aforementioned Patent Documents 1 and 2. Specific examples of $R^1(R^1)NH$ include primary amines, secondary amines, and tertiary amines (including cyclic amines) such as methylamine, dimethylamine, ethylamine, diethylamine, propylamine, dipropylamine, butylamine, dibutylamine, pentylamine, dipentylamine, hexylamine, dihexylamine, benzylamine, dibenzylamine, aziridine, azetidine, pyrrolidine, piperidine, morpholine, 1-(tert-butoxycarbonyl)piperazine, hexahydro-1H-azepine, 1-(tert-butoxycarbonyl)homopiperazine, octahydroazocine, and octahydro-1H-azonine.

EXAMPLES

The present invention is hereinafter described specifically by means of the following Examples, which, however, are not to be construed as limiting the present invention in any way.

Example 1

Synthesis of 6-(benzylthio)isoquinoline (4)

Benzylmercaptan (5.45 g) was dissolved in dimethyl sulfoxide (80 mL), potassium tert-butoxide (4.92 g) was added little by little at room temperature, and the mixture was stirred for 20 minutes. Subsequently, 6-bromoisoquinoline (2) (6.1 g) was added, and the mixture was stirred at 100° C. for 3 hours. The temperature was returned to room temperature, water (600 mL) was added, the mixture was extracted with ethyl acetate, and the extract was dried using anhydrous sodium sulfate. After the dry matter was filtered and concentrated under reduced pressure, an appropriate amount of hexane was added to the resulting oily crude product for crystallization. The resulting crystal was washed with hexane, and the solid was separated by filtration to obtain 6-(benzylthio)isoquinoline (6.29 g, percent recovery 85%). $^1$H NMR (500 MHz, CDCl$_3$, δ ppm): 4.29 (s, 2H), 7.26-7.33 (m, 3H), 7.38-7.40 (m, 2H), 7.46-7.49 (m, 2H), 7.59 (s, 1H), 7.82 (d, 1H, J=8.5 Hz), 8.47 (d, 1H, J=6.0 Hz), 9.15 (s, 1H). Melting point: 80° C.

Example 2

Synthesis of isoquinoline-6-sulfonyl chloride hydrochloride (5a) from 6-(benzylthio)isoquinoline (4)

6-(Benzylthio)isoquinoline (5 g) was dissolved in acetic acid (7.5 mL), water (5 mL), and acetonitrile (200 mL), and 1, 3-dichloro-5, 5-dimethylhydantoin (7.9 g) was gradually added little by little at 0° C. After stirring at 5° C. or lower for 2 hours, methyl tert-butyl ether (200 mL) was added. Subsequently, a 4M hydrochloric acid/1,4-dioxane solution (5 mL) was added, and the mixture was stirred for 30 minutes. The precipitated solid was isolated by filtration and washed with an appropriate amount of methyl tert-butyl ether to obtain isoquinoline-6-sulfonyl chloride hydrochloride as a white solid (4.50 g, percent recovery 85%). $^1$H NMR (500 MHz, DMSO-d$_6$, δ ppm): 8.16 (d, 1H, J=8.5 Hz), 8.50-8.53 (m, 2H), 8.61 (d, 1H, J=6.5 Hz), 8.67 (d, 1H, J=6.5 Hz), 9.88 (s, 1H). Melting point: 102° C. (decomposed).

FIG. 1 shows an actual $^1$H NMR chart. As is evident from FIG. 1, no impurity peak was found but the desired product.

Example 3

Synthesis of isoquinoline-6-sulfonyl chloride hydrochloride (5a) from 6-aminoisoquinoline (3)

Figure 2:
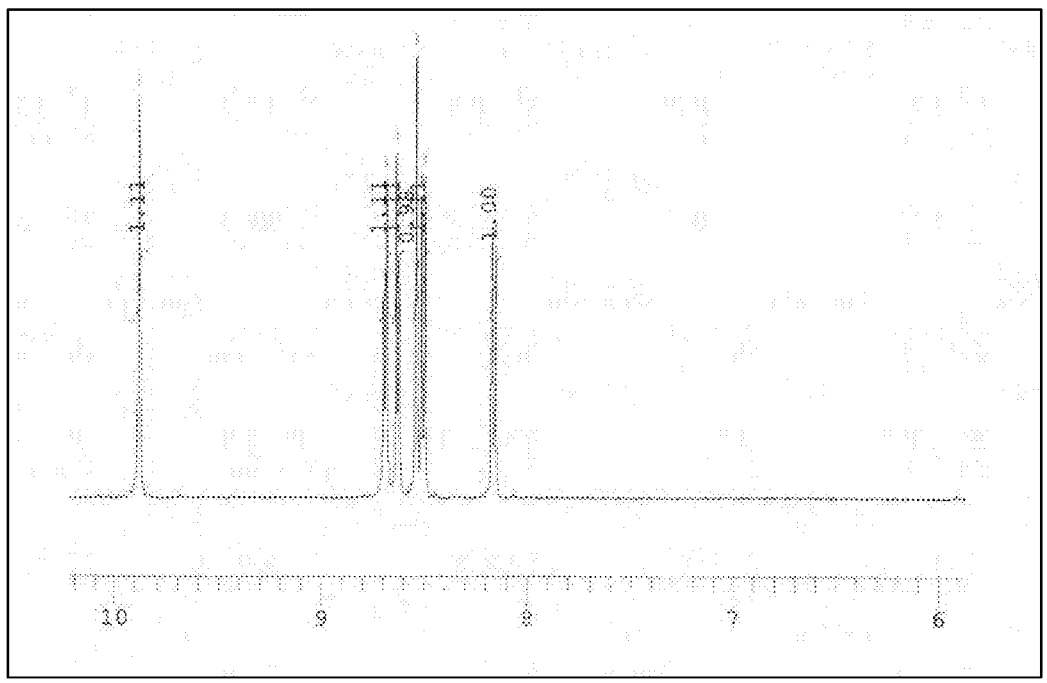
FIG. 2 shows a $^1$H NMR chart of the isoquinoline-6-sulfonyl chloride hydrochloride obtained in Example 3.

6-Aminoisoquinoline (500 mg) was dissolved in concentrated hydrochloric acid (10 mL) at 0° C., sodium nitrite (260 mg) dissolved in water (1 mL) was gradually added, and the mixture was stirred at 0° C. for 15 minutes. This solution was gradually added at 0° C. to a solution, which was prepared by adding thionyl chloride (1.1 mL) to a mixed solution of acetic acid (4 mL) and water (2 mL) at 0° C. and subsequently adding copper chloride (35 mg), and the mixture was stirred for 1 hour. An appropriate amount of dichloromethane was added, and sodium hydrogen carbonate (13 g) and water were added alternatively to neutralize the mixture. Insoluble components were removed by Celite filtration, and the resulting filtrate was extracted with dichloromethane. After being dried using anhydrous sodium sulfate, the extract was filtered, and a 2M hydrochloric acid/diethyl ether solution (6 mL) was added to the resulting solution at 0° C., and an appropriate amount of diethyl ether was added. The precipitated solid was isolated by filtration and washed with an appropriate amount of diethyl ether to obtain isoquinoline-6-sulfonyl chloride hydrochloride as a light-yellow solid (484 mg, percent recovery 52%). The $^1$H NMR peak and melting point values agreed with those obtained in Example 2. FIG. 2 shows an actual $^1$H NMR chart. As is evident from FIG. 2, no impurity peak was found but the desired product.

Example 4

Synthesis of isoquinoline-6-sulfonyl chloride hydrobromide (5b) from 6-(benzylthio)isoquinoline (4)

6-(Benzylthio)isoquinoline (4) (1 g) was reacted under the same conditions as Example 2, but with hydrobromic acid added in place of hydrochloric acid, to obtain isoquinoline-6-sulfonyl chloride hydrobromide (1.04 g, percent recovery 84%). The $^1$H NMR data showed that this reaction yielded the desired product as a single compound.

Example 5

Synthesis of isoquinoline-6-sulfonyl chloride sulfate (5c) from 6-(benzylthio)isoquinoline (4)

6-(Benzylthio)isoquinoline (4) (1 g) was reacted under the same conditions as Example 2, but with sulfuric acid added in place of hydrochloric acid, to obtain isoquinoline-6-sulfonyl chloride sulfate (944 mg, percent recovery 72%). The $^1$H NMR data showed that this reaction yielded the desired product as a single compound.

Example 6

Synthesis of isoquinoline-6-sulfonyl chloride phosphate (5d) from 6-(benzylthio)isoquinoline (4)

6-(Benzylthio)isoquinoline (4) (1 g) was reacted under the same conditions as Example 2, but with phosphoric acid added in place of hydrochloric acid, to obtain isoquinoline-6-sulfonyl chloride phosphate (872 mg, percent recovery 67%). The $^1$H NMR data showed that this reaction yielded the desired product as a single compound.

Reference Example 1

Synthesis of isoquinoline-6-sulfonyl chloride (1) from 6-aminoisoquinoline (3)

With the use of 6-aminoisoquinoline (280 mg), the reaction was carried out under the conditions described in Patent Document 1. After completion of the reaction, extraction, concentration under reduced pressure, and purification by silica gel column chromatography were performed, to obtain isoquinoline-6-sulfonyl chloride (35 mg, percent recovery 8%). $^1$H NMR (500 MHz, CDCl$_3$, ? ppm): 8.01 (d, 1H, J=5.0 Hz), 8.23 (d, 1H, J=10 Hz), 8.38 (d, 1H, J=10 Hz), 8.66 (s, 1H), 8.79 (d, 1H, J=5.0 Hz), 9.59 (s, 1H).

Reference Example 2

Synthesis of isoquinoline-6-sulfonyl chloride (1) from 6-(benzylthio) isoquinoline (4)

Figure 3:
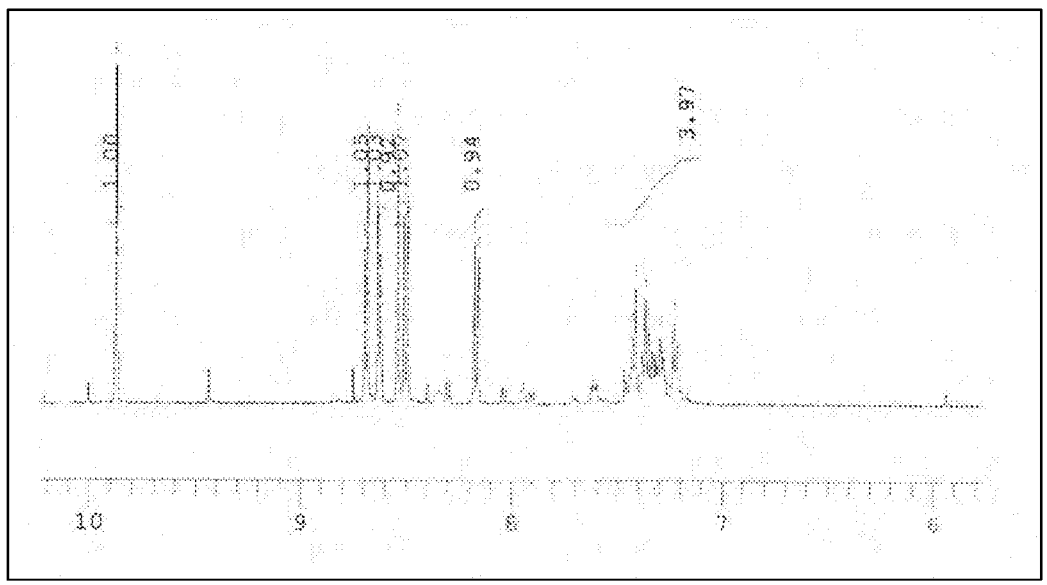
FIG. 3 shows a $^1$H NMR chart of the isoquinoline-6-sulfonyl chloride obtained in Reference Example 2.

With the use of 6-(benzylthio)isoquinoline (1 g), the reaction was carried out under the same conditions as Example 2. After completion of the reaction, the solvent was concentrated under reduced pressure. Dichloromethane was added, and a 5% aqueous solution of sodium hydrogen carbonate was added at 0° C. The mixture was extracted with dichloromethane, and the extract was dried using anhydrous sodium sulfate. The resulting dry matter was concentrated under reduced pressure to obtain a crude product of isoquinoline-6-sulfonyl chloride (1.39 g). FIG. 3 shows an actual $^1$H NMR chart. As is evident from the chart, a peak of the desired product compound (1) was found, and impurity peaks were also found.

Reference Example 3

Synthesis of isoquinoline-6-sulfonyl chloride (1) from 6-aminoisoquinoline (3)

Figure 4:
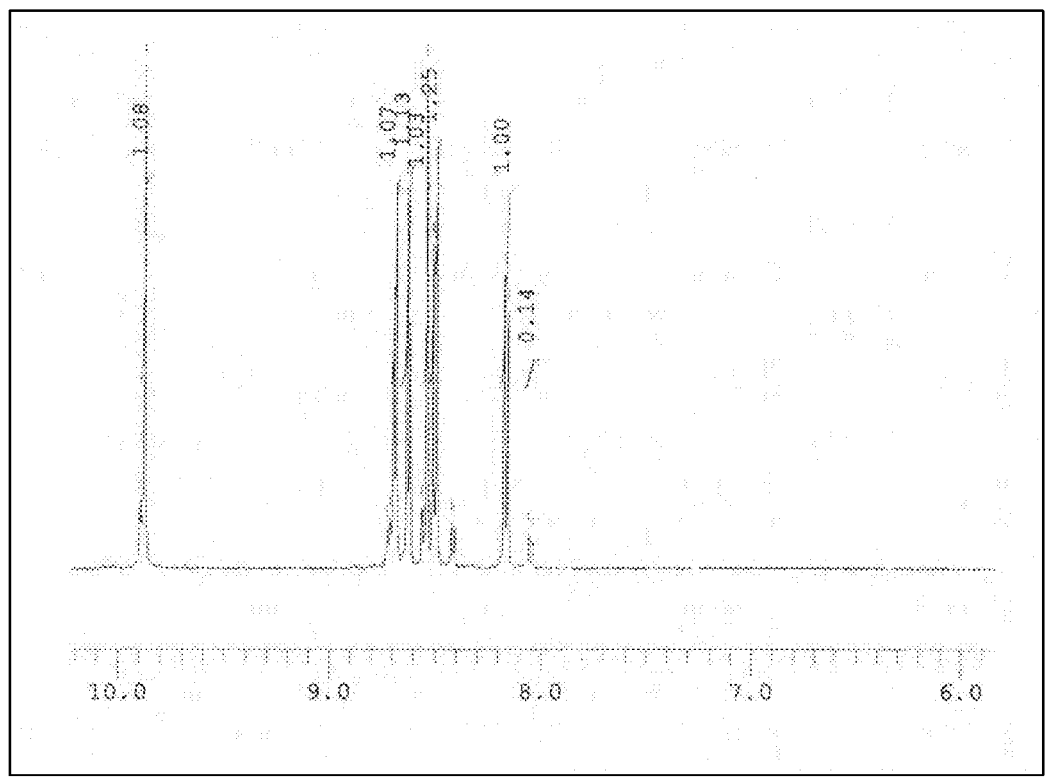
FIG. 4 shows a $^1$H NMR chart of the isoquinoline-6-sulfonyl chloride obtained in Reference Example 3.

With the use of 6-aminoisoquinoline (500 mg), the reaction was carried out under the same conditions as Example 3. After completion of the reaction, extraction and drying were performed, and the resulting solution was concentrated to obtain a crude product of isoquinoline-6-sulfonyl chloride (1) (367 mg). FIG. 4 shows an actual $^1$H NMR chart. As is evident from the chart, a peak of the desired product compound (1) was found, and impurity peaks were also found.

Test Example 1

Behavior of Compound (1) on Silica Gel TLC Plate

A teaspoonful of a white solid of highly pure isoquinoline-6-sulfonyl chloride hydrochloride (5a) as obtained in Example 2 or 3 was placed in a microtube and suspended in an appropriate amount of ethyl acetate. Subsequently, a saturated aqueous solution of sodium hydrogen carbonate was added to prepare a transparent solution in two layers, and the free form of isoquinoline-6-sulfonyl chloride was dissolved in the upper organic layer. Only a 2 cm of the solvent was aspirated from the organic layer using a glass capillary, the compound (1) solution was spotted near one corner of a 5-cm square TLC plate, the plate was allowed to stand in a developing vessel containing an appropriate amount of methyl tert-butyl ether, and a chromatogram was developed until the solvent reached close to the upper portion of the TLC plate. After chromatogram development, the plate was dried, and the position of the compound (1) spot was determined by ultraviolet exposure (left panel of FIG. 5). After being allowed to stand for 10 minutes, the TLC plate was rotated by 90 degrees, and the compound (1) spot was developed again. After chromatogram development, the plate was dried, and the position of the compound (1) spot was determined by ultraviolet exposure (right panel of FIG. 5).

Figure 5:
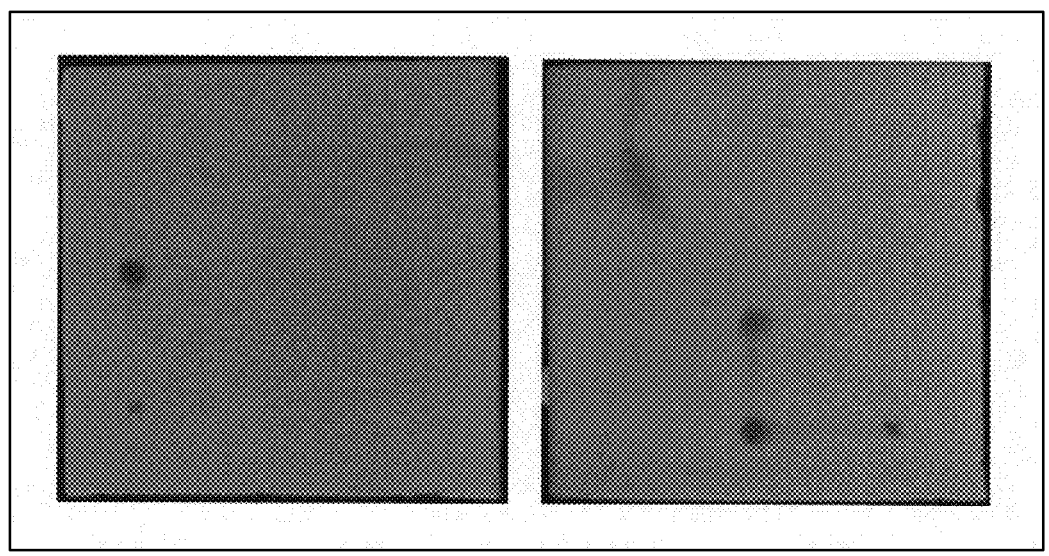
FIG. 5 shows the behavior of isoquinoline-6-sulfonyl chloride on a silica gel TLC plate.

As seen from FIG. 5, the spot of compound (1) obtained after chromatogram development just following spotting gave a single spot consisting generally of compound (1), whereas a large spot distinct from compound (1) appeared near the origin on the TLC plate subjected to a second development after being allowed to stand for 10 minutes, and the amount of compound (1) decreased; it was suggested that compound (1) had been decomposed or degraded on the silica gel. This result was consistent with the result in Reference Example 1 that the percent recovery decreased extremely as compound (1) was purified by silica gel column chromatography.

Test Example 2

An elemental analysis of isoquinoline-6-sulfonyl chloride hydrochloride (5a), the compound of the present invention, as obtained in Examples 2 and 3 gave the following results. Figures in parentheses are calculated values.

Isoquinoline-6-sulfonyl chloride hydrochloride (5a) C, 41.0% (40.93%); H, 2.87% (2.67%); N, 5.38% (5.30%)

Test Example 3

Figure 6:
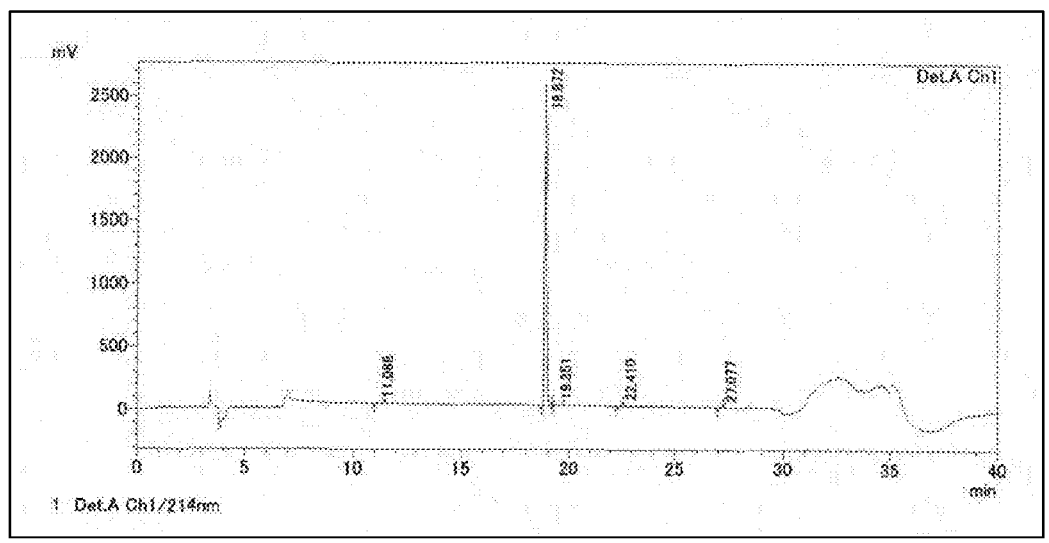
FIG. 6 shows an HPLC chart of a sulfonamide compound obtained using isoquinoline-6-sulfonyl chloride hydrochloride.

The compound of the present invention, i.e., isoquinoline-6-sulfonyl chloride hydrochloride (5a), was reacted with an amine compound, and the resulting crude product was analyzed by HPLC for reaction selectivity, impurity content, and other aspects of the compound (5a) of the present invention. Specifically, an appropriate amount of the compound (5a) of the present invention and an appropriate amount of n-butylamine were reacted by being mixed in 1 mL of dichloromethane in the presence of an appropriate amount of triethylamine. Several minutes later, a portion of the reaction solution was sampled and analyzed by HPLC (FIG. 6). As a result, a sulfonamide compound as a single substance was produced. It was also found that the contents of by-products, impurities, and other substances were extremely low.

The above-described results show that isoquinoline-6-sulfonyl chloride hydrochloride (5a), the compound of the present invention, is of high purity and has quality that makes the compound to be adequately useful in the reaction with an amine compound.

The invention claimed is:

1. A method for manufacturing isoquinoline-6-sulfonyl chloride and/or one or more acid addition salts thereof, the method comprising:
    subjecting 6-(benzylthio)isoquinoline to an oxidative chlorination reaction.

2. A method for manufacturing an isoquinoline-6-sulfonyl chloride acid addition salt, the method comprising:
    reacting 6-aminoisoquinoline with a nitrite or nitrous acid ester, then with thionyl chloride, and then with an acid.

3. 6-(Benzylthio)isoquinoline.

4. The method of claim 2, wherein the reacting of the 6-aminoisoquinoline employs the nitrite.

5. The method of claim 2, wherein the reacting of the 6-aminoisoquinoline employs the nitrous acid ester.

6. The method of claim 1, wherein the oxidative chlorination reaction comprises contacting the 6-(benzylthio)isoquinoline with an oxidative chlorinating agent comprising 1,3-dichloro-5,5-dimethylhydantoin, sulfuryl chloride, N-chlorosuccinimide, gaseous chlorine, and/or sodium hypochlorite.

7. The method of claim 1, wherein the oxidative chlorination reaction comprises contacting the 6-(benzylthio)isoquinoline with 1,3-dichloro-5,5-dimethylhydantoin.

8. The method of claim 1, wherein the oxidative chlorination reaction comprises contacting the 6-(benzylthio)isoquinoline with sulfuryl chloride.

9. The method of claim 1, wherein the oxidative chlorination reaction comprises contacting the 6-(benzylthio)isoquinoline with N-chlorosuccinimide.

10. The method of claim 1, wherein the oxidative chlorination reaction comprises contacting the 6-(benzylthio)isoquinoline with gaseous chlorine.

11. The method of claim 1, wherein the oxidative chlorination reaction comprises contacting the 6-(benzylthio)isoquinoline with sodium hypochlorite.

12. The method of claim 1, wherein the oxidative chlorination reaction is carried out in a solvent comprising acetic acid, acetonitrile, and/or water.

13. The method of claim 1, wherein the oxidative chlorination reaction is carried out in a solvent comprising acetic acid.

14. The method of claim 1, wherein the oxidative chlorination reaction is carried out in a solvent comprising acetonitrile.

15. The method of claim 1, wherein the oxidative chlorination reaction is carried out in a solvent comprising water.

16. The method of claim 1, wherein the oxidative chlorination reaction is carried out at room temperature or lower.

17. The method of claim 1, wherein the oxidative chlorination reaction is carried out for a reaction time in a range of from 1 to 5 hours.

\* \* \* \* \*